US00PP15474P2

(12) United States Plant Patent
Berry

(10) Patent No.: US PP15,474 P2
(45) Date of Patent: Jan. 11, 2005

(54) ***LIRIOPE MUSCARI* PLANT NAMED 'BIGUN'**

(50) Latin Name: *Liriope muscari*
Varietal Denomination: Bigun

(75) Inventor: James Bryan Berry, Daphne, AL (US)

(73) Assignee: Plant Development Services Inc., Loxley, AL (US)

( * ) Notice: Subject to any disclaimer, the term of this patent is extended or adjusted under 35 U.S.C. 154(b) by 32 days.

(21) Appl. No.: 10/822,164

(22) Filed: Apr. 12, 2004

(51) Int. Cl.[7] ..... A01H 5/00
(52) U.S. Cl. ..... Plt./263
(58) Field of Search ..... Plt./263

(56) References Cited

U.S. PATENT DOCUMENTS

PP12,068 P2 * 8/2001 Jacobs ..... Plt./263
2004/0034894 P1 * 2/2004 Love ..... Plt./263

* cited by examiner

*Primary Examiner*—Kent Bell
*Assistant Examiner*—W C Haas

(57) ABSTRACT

A new and distinct variety of *Liriope* plant named 'Bigun' found as an openly pollinated seedling of *Liriope muscari* 'Big Blue'. The new variety is characterized by its wide, slightly twisted, dark green foliage, and attractive dark violet flowers.

1 Drawing Sheet

*Liriope muscari.*
Varietal denomination: 'Bigun'.

BACKGROUND OF THE INVENTION

This new *Liriope* variety named 'Bigun' was found as a plant within the progeny of a controlled open pollination of *Liriope muscari* 'Big Blue', an unpatented variety, maintained in a private nursery in Loxley, Ala. The seedling was discovered by James Bryan Berry in June, 1996. The new and distinct *Liriope muscari* plant of this invention comprises a novel and valuable *Liriope* plant with wide, slightly twisted, dark green foliage, and attractive dark violet flowers.

Asexual propagation of the new plant by division has been under Mr. Berry's direction at the same location. The new plant retains its distinctive characteristics and reproduces true to type in successive generations. The plant cannot be reproduced true from seed.

SUMMARY OF THE INVENTION

The following are the most outstanding and distinguishing characteristics of this new cultivar when grown under normal horticultural practices in Loxley, Ala.

1. Attractive dark violet flowers are fragrant, profuse and produced on long racemes.
2. Foliage is dark green year round.
3. Fast growth rate under normal fertilization and moisture conditions.
4. Form is grasslike with wide, slightly twisted leaves.
5. Easily propagated by division.
6. Heat and drought resistant.
7. Good groundcover.
8. Tolerates full sun to shade.
9. Desirable in planters.
10. Effective in mass.
11. Withstands wind and salt spray.

12. An excellent plant for borders.
13. Hardy to Zone 7.

DESCRIPTION OF THE DRAWINGS

This new *Liriope muscari* variety is illustrated by the accompanying photographic prints in which:

1. The photograph at the top of the sheet is a close-up of the new variety 'Bigun' showing the attractive foliage and flowers.

2. The photograph at the bottom of the sheet is a side-by-side photograph of (from left to right) *Liriope muscari* 'Bigun', *Liriope muscari* 'Big Blue', and *Liriope gigantea* 'Merton Jacobs' U.S. Plant Pat. No. 12,068. This photograph, which was taken in early July, shows the violet flowers on long racemes and the slightly twisted foliage of the new variety.

The colors shown are as true as is reasonably possible to obtain by conventional photographic procedures. Colors in the photograph may appear different than actual colors due to light reflectance. The colors of the various plant parts are defined with reference to The Royal Horticultural Society Colour Chart. Description of colors in ordinary terms are presented where appropriate for clarity in meaning.

BOTANICAL DESCRIPTION OF THE PLANT

The following is a detailed description of the new variety of *Liriope* based on observations made in wholesale commercial production practices, in greenhouses, and in established landscape plantings in Loxley, Ala. This information was obtained from two year old plants grown in three gallon containers and one year old plants grown in one gallon containers.

Distinctive Characteristics

TABLE 1

| Characteristic | *Liriope muscari* 'Bigun' | *Liriope muscari* 'Big Blue' | *Liriope gigantea* 'Merton Jacobs' PP #12068 |
|---|---|---|---|
| Height (Mature) | 18–24" | 18–20" | 24–30" |
| Width (Mature) | 18–24" | 18–20" | 24–30" |
| Bloom Period | Mid June–July | Late June–July | Aug–Sept |
| Bloom Color | Violet Blue G. 92A | Violet Blue G. 91A | Violet Blue G. 85B |
| Raceme Length | 12–18" | 12–14" | 14–18" |
| Leaf Length | 14–18" | 14–18" | 1–3' |
| Leaf Width | ½–¾" | ¼–7/16" | 5/16–7/16" |
| Leaf Curvature | Slightly twisted | Almost Flat | Almost Flat |

*Liriope* 'Bigun' is similar to the parent cultivar *Liriope* 'Big Blue', however, in side-by-side comparisons conducted in Loxley, Ala., 'Bigun' blooms 7–10 days earlier and has a wider leaf which is slightly twisted.

*Liriope gigantea* 'Merton Jacobs' U.S. Plant Pat. No. 12,068 is well known in the nursery industry and differs from the new variety in that it is more upright growing plant and blooms later in the year.

Classification
Botanical: *Liriope muscari* 'Bigun'.
Form: Dense, grasslike clump.
Height: 18–24".
Width: 18–24".
Growth habit: Dense, grasslike clump. Fast growth rate under normal fertilization and moisture conditions.
Growth rate: In a period of three years from a division, under normal growing conditions in Loxley, Ala., the plant reaches a height of 12 to 14" and a spread of 12 to 14". Many leaves arise from a central crown resulting in a dense habit.
Foliage: Evergreen, grasslike, basal, rhizomatous, coriaceous, narrowly linear, firm, arching, slightly twisted, long alternate, ½" to ¾" wide by 14 to 18" long. Leaves are numerous and leaf veination is parallel. Margins are smooth. The upper surface of the immature leaves is Green Group 143A, glossy and glabrous. The underside is Green Group 137C and matte. The veins are Green Group 137A and between the veins are Green Group 137D. The upper surface of the mature leaves is Green Group 137A, glossy and glabrous and the underside remains Green Group 137C and matte. The base of the leaves is Yellow-Green Group 145A.

Like the parent cultivar, 'Bigun' has no above ground stems. It grows by adding bibs or small clumps of leaves on short rhizomes on the side of the existing clump. The rhizomes are normally less than one inch long. As the plant grows, the clump becomes larger and can be propagated by separating the bibs. Sections of the fibrous root system often enlarge and function as food storage organs. These rhizomes are ½ to ¾" long, ¼ to ½" wide, Yellow-White Group 158B and are not useful for propagation.

In 2000, the date of initial spring growth was March 2, in Loxley, Ala. After the initial spring flush, there was almost continuous growth until fall, ending November 11, also in Loxley, Ala. This growth pattern was identical to the parent cultivar.

Flowers: Perfect, fragrant, in axillary fascicles arranged in terminal racemes. The flowers and mature buds are Violet-Blue Group 92A. The pedicel is 1/16 to ⅛" long and Violet-Blue Group 92B. Immature buds are Violet-Blue Group 92B. There are six to eight elliptical petals which are 3/16" long and 1/16 to ⅛" wide. No sepals are produced. The six stamens are 1/32 to 1/16" long and the superior ovary is 1/16 to 3/32" long. The pollen is Yellow Group 6B. Flowers are bourne on racemes in clusters of 3 to 5, which are open from the base to the apex and are held high in the foliage. Each cluster emerges from a bract which is Green Group 143C. The racemes are 12 to 18" long and have a 1/16 to ⅛" diameter. These racemes are Purple Group 79C at the base and Purple Group 86D near the apex. There is a six to eight week flowering period normally beginning in mid June in Loxley, Ala. A mature plant may have 50 or more racemes producing several hundred flowers. Flowers have a sweet fragrance.
Fruit: Berrylike drupe, globose, 3/16 to 5/16" diameter, containing one or two seeds. Seeds are ⅛" to ¼" in diameter, globose, and Greyed-Green Group 195D. Immature fruit are Yellow-Green Group 144A maturing to Green Group 139A. In the late fall and early winter the fruit turn Black Group 202A and fall off. Fruit set may be heavy.
Culture: Grows well in a wide range of conditions and tolerates sun to shade. Grows in nearly any soil type, from moist to dry and sand to clay. Very heavy clays should be amended with peat moss, compost, or shredded pine bark to improve the soil texture. Poorly drained locations should be avoided. Responds well to mulching and medium applications of fertilizer; prefers ph 6 to 7. Adaptable to containers and above ground planters. Tolerates wind and salt spray. Propagated by division any time of year. Cold-hardiness and resistance to drought are comparable to the parent cultivar.
Disease and insect resistance: Resistance to diseases and insects common to plants of *Liriope* has not been observed.

I claim:

1. A new and distinct variety of *Liriope* plant named 'Bigun', as illustrated and described.

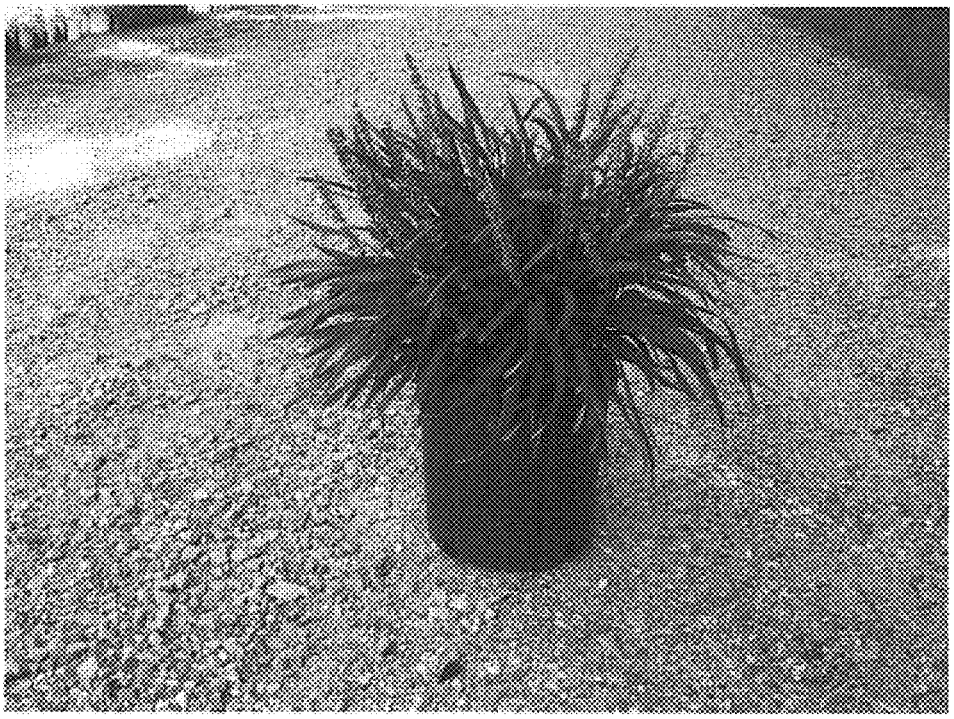
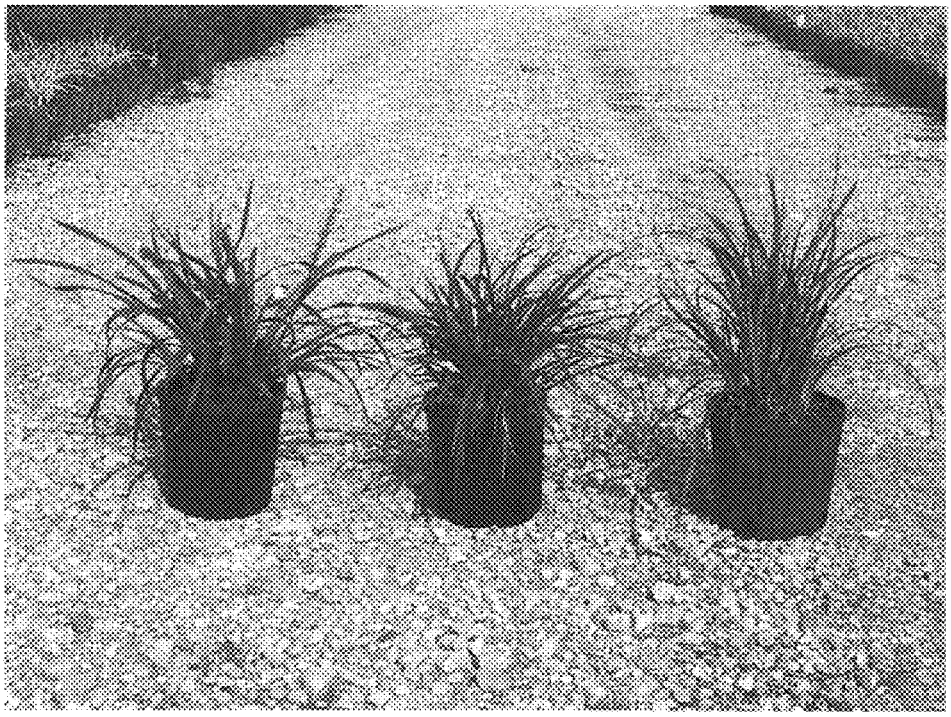

* * * * *